United States Patent [19]

Kagan et al.

[11] Patent Number: 4,997,854

[45] Date of Patent: Mar. 5, 1991

[54] ANTI-FIBROTIC AGENTS AND METHODS FOR INHIBITING THE ACTIVITY OF LYSYL OXIDASE IN-SITU USING ADJACENTLY POSITIONED DIAMINE ANALOGUE SUBSTRATES

[75] Inventors: Herbert M. Kagan, Arlington; Stephen N. Gacheru, Worcester, both of Mass.

[73] Assignee: Trustees of Boston University, Boston, Mass.

[21] Appl. No.: 398,672

[22] Filed: Aug. 25, 1989

[51] Int. Cl.$^5$ ............................................. A61K 31/13
[52] U.S. Cl. .................................................. 514/660
[58] Field of Search ......................................... 514/660

[56] References Cited

PUBLICATIONS

*The Journal of Biological Chemistry* (vol. 254(16) pp. 7831–7836).
Chemical Abstracts (vol. 107): 35572t (1987).
Chemical Abstracts (vol. 105:221604p) (1986).

*Primary Examiner*—Stanley D. Friedman
*Assistant Examiner*—Kevin E. Weddington
*Attorney, Agent, or Firm*—David Prashker

[57] ABSTRACT

A class of anti-fibrotic agents and methods for their use as effective inhibitor substrate analogues of lysyl oxidase in-situ are provided. The inhibitory substrate analogues comprise adjacently positioned diamine compositions which may be employed in-vivo to therapeutically treat a wide variety of different pathological fibrotic diseases, disorders, and abnormalities.

6 Claims, 5 Drawing Sheets

ANTI-FIBROTIC AGENTS AND METHODS FOR INHIBITING THE ACTIVITY OF LYSYL OXIDASE IN-SITU USING ADJACENTLY POSITIONED DIAMINE ANALOGUE SUBSTRATES

RESEARCH SUPPORT

The research investigations for the present invention were supported by National Institute of Health Grants R37-AR-18880 and HL-19717.

FIELD OF THE INVENTION

The present invention is directed to anti-fibrotic agents useful in controlling pathological fibrotic states in a variety of different clinical disorders, diseases, and abnormalities; and is particularly directed to methods for effectively inhibiting the enzymatic activity of lysyl oxidase in-situ using adjacently positioned diamine analogue substrates.

BACKGROUND OF THE INVENTION

Pathological fibrotic states are clinically apparent abnormalities caused by the proliferation of fibroblasts, smooth muscle and other fibrogenic cells; and by the laying down of collagen and other extracellular elements typical of wound healing within specific tissues and organs of the body. The pathology is not only the abnormally excess formation of collagen polypeptide alpha chains, but also the critical modification using the enzyme lysyl oxidase to create cross-linkages between adjacent collagen chains and collagen molecules which is the basis of the structural stability, maturation, and strength of collagen and scar tissue in general. The cross-linking of the individual collagen alpha chains is the major contributor to the tensile strength of the cross-linked fibrils. Depending upon the location of the collagen chain formation and its cross-linking via the enzyme lysyl oxidase, the abnormalities may take form in a variety of clinically identifiable and diagnosed conditions including: lung fibrosis, atherosclerosis, keloid, liver fibrosis, scar tissue formation, diabetes, tumor development, and even post-operatively in procedures such as radial keratotomy where scar formation is counter productive to the purposes of the surgery. For more detailed information and review of the relationship between the enzyme lysyl oxidase and the creation of the pathological fibrotic state, the following publications are recommended. [Kagan et al., *Arteriosclerosis* 1:287-291 (1981); Chichester et al., *Am. Rev. Respir. Dis.* 124:709-713 (1981); Lerman et al., *Circ. Res.* 53:378-388 (1983); Levene et al., *Brit. J. Exp. Path.* 49:152-159 (1968); Kogan, L. L. and L. Katzen, *Ann. Ophthal.* 15:842-845 (1983); Chvapil, M., *Life Sciences* 16:1345-1362 (1975) Arem, A. J. and R. Misiorowski, *J. Med.* 7:239-248 (1976); and Knapp et al., *Am. J. Pathol.* 86:47-70 (1977)].

For these reasons, there has been considerable interest and research investigations into the enzymatic activity and properties of lysyl oxidase and its potential inhibition to prevent collagen chain cross-linking. It has been proposed that by preventing the oxidative deamination of lysine and hydroxylysine amino groups within the collagen alpha chains, which is the enzymatic function and specific activity of lysyl oxidase, the physical properties of the collagen scar tissue and the resulting fibrotic pathological state could be substantially reduced. Much of the original interest and research centered around the pathological defect found in Marfan's Syndrome, in which a decreased formation of cross-linkages within collagen and elastin fibers occurs. In prepared animal models, live rats fed sweet pea meal derived from the seeds of *Lathyrus odoratus* developed remarkably similar collagen cross-linking defects and skeletal abnormalities. The active ingredient responsible for the production of this defective cross-linking collagen fiber condition or "Lathyrism" was found to be beta-aminopropionitrile, which blocks cross-linkages in collagen and elastin fibers by inhibiting the enzyme lysyl oxidase. [Page R. C. and E. P. Benditt, *Biochemistry* 6:1142-1147 (1976) and *Proc. Soc. Exp. Biol. Med.* 124:454-459 (1967); Narayanan et al., *Biochem. Biophys. Res Commun.* 46:745-751 (1971)]. Until very recently, it was believed that the enzymatic activity of lysyl oxidase required the presence of both metallic copper; and a specific cofactor, pyridoxal phosphate [Murray, J. C. and C. R. Levene, *Biochem. J.* 167:463-467 (1977); Murray et al., *Exp. Mol. Pathol.* 28:301-308 (1978)]. Using this enzyme model, a number of other inhibitors of lysyl oxidase in addition to beta-aminopropionitrile were reported: Carbonyl Reagents [Harris et al., *Biochem. Biophys. Acta* 341:332-334 (1973); Kagan et al., *Biochim. Biophys. Acta* 365:223-234 (1974)]; isoniazid [Arem, A. J. and R. L. Misiorowski, *J. Med.* 7:239-247 (1976)]; Iproniazid [Rucker, R. B. and B. L. O'Dell, *Biochim. Biophys. Acta* 22:527-529 (1970)]; and dithiothreitol [Harris et al., *Biochem. Biophys. Acta* 341:332-334 (1973)]. More recently, an investigation of lysyl oxidase inhibition revealed that this enzyme in the presence of copper ion and the bound carbonyl cofactor was also inhibited by disulfhydryls, sulfhydryl-amines, and penicillamine in an irreversible manner. In addition, reversible inhibition was reported using dithiothreitol, 1,3-dithio-2-propanol, and 1,3-diaminopropane [Misiorowski, R. L. and N. J. Werner, *Biochem. Biophys. Res. Comm.* 85:809-814 (1978)].

Within the last few years, however, it was recognized that the lysyl oxidase enzyme cofactor was not, as previously believed, pyridoxal phosphate - but instead was pyrroloquinoline quinone (hereafter "PQQ") [Williamson et al., *J. Biol. Chem.* 261:16302-16305 (1986); Kagan et al., *1st International Symposium On PQQ And Quinoproteins*, Delft, The Netherlands, Sept. 5-7, 1988, page 57; and Kagan, H. M., Abstract, *International Congress On Elastin: Chemical And A Biological Aspects*. Universita Della Basilicata, Potenza, Italy, Oct. 10-13, 1988]. This in turn has generated increased interest within the relevant components of the scientific community concerning the mode of action of the previously reported inhibitors of lysyl oxidase. In addition, because many of the previously reported compositions were not suitable for clinical and/or therapeutic use in living humans, there remains a long standing and continuing need for compositions which are effective inhibitors of lysyl oxidase in-situ, be it for human or for animal therapeutic use.

SUMMARY OF THE INVENTION

A method for inhibiting the enzymatic activity of lysyl oxidase in-situ is provided, said method comprising the steps of:

obtaining at least one inhibitory analogue substrate composition having the formula

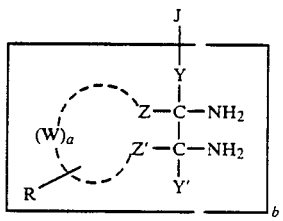

Wherein a is 0 or 1 and b is at least 1;

Y and Y' individually may be omitted entirely but when present is selected from the group consisting of hydrogen, a halogen, a hydrocarbon entity, and a substituted hydrocarbon entity;

Z and Z' individually may be omitted entirely but when present are individually selected from the group consisting of hydrogen, a halogen, a hydrocarbon entity, a substituted hydrocarbon entity, and link R when W is absent;

W may be omitted entirely but when present comprises the number of atoms necessary to form a saturated or unsaturated cyclic structure;

R may be omitted entirely, but when present is a moiety able to react with another ligand; and J may be omitted entirely but when present is any organic moiety joining the diamine composition to another molecule as a copolymer.

The present invention also includes therapeutic methods for using the inhibitory analogue substrate composition as a anti-fibrotic agent in-vivo for therapeutic treatment of living subjects afflicted with fibrotic diseases, disorders, and pathologies.

DETAILED DESCRIPTION OF THE FIGURES

The present invention may be more easily and completely understood when taken in conjunction with the accompanying drawing, in which.

DETAILED DESCRIPTION OF THE PREFERRED EMBODIMENTS

Figure 1A:
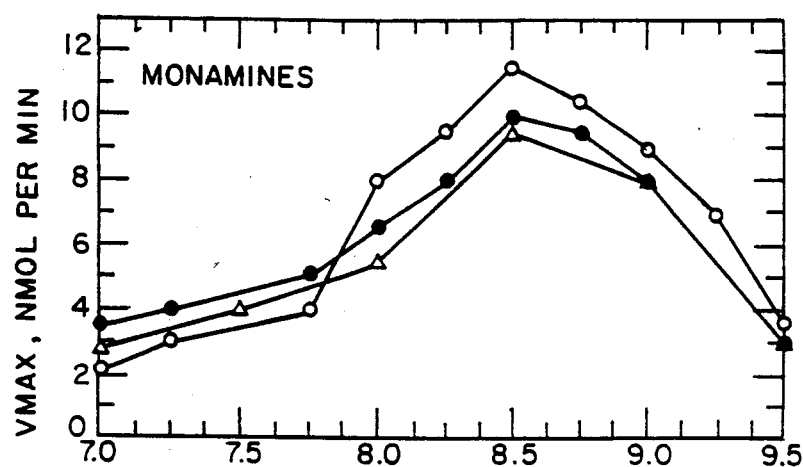
FIGS. 1A and 1B are graphs illustrating the pH dependent oxidation of monoamines and diamines by lysyl oxidase.

The present invention provides a class of highly effective anti-fibrotic agents; and methods for using this class of anti-fibrotic agents as effective analogue substrate inhibitors of lysyl oxidase in-situ - that is, under both in-vitro and in-vivo conditions.

The most general structural formula for the lysyl oxidase inhibitory analogue substrates as a class is provided by Formula I as follows:

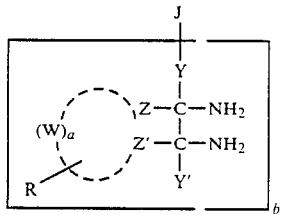

wherein a is 0 or 1, and wherein b is at least 1;

Y and Y' individually may be omitted entirely, but when present are individually selected from the group consisting of hydrogen, a halogen, a hydrocarbon entity, and a substituted hydrocarbon entity;

Z and Z' individually may be omitted entirely but when present are selected from the group consisting of hydrogen, a halogen, a hydrocarbon entity, a substituted hydrocarbon entity, and links R when W is absent;

W may be omitted entirely, but when present comprises the number of atoms necessary to form a saturated or unsaturated cyclic structure;

R may be omitted entirely, but when present is a moiety able to react with another ligand; and J may be omitted entirely, but when present is any organic moiety linking the diamine composition to another molecule as a copolymer.

It will be recognized and appreciated that this inhibitory class of analogue substrates for lysyl oxidase offer a variety of advantages to the user, which include:

(a) Synthesis methods for the defined chemical class as a whole which are conventionally known, relatively simple to perform, and provide the desired diamine in high yield;

(b) Purification of the diamines conforming to Formula I is easy to perform using conventionally known techniques and apparatus;

(c) The diamines of Formula I are stable compositions able to be prepared in a pharmaceutically acceptable manner in both sterile and non-sterile formats.

(d) The diamines are generally very soluble in aqueous systems at neutral pH, thereby facilitating their administration in-vivo.

Given the broad class definition of Formula I, the preferred inhibitory embodiments are those listed in Table I below.

TABLE I

| Preferred Linear Diamines |
|---|
| ethylenediamine |
| 1,2-diaminopropane |
| 1,2-diaminobutane |
| 3,4-diaminobutane |
| 1,2-diaminooctane |
| 7,8-diaminooctane |
| Preferred Branched Diamines |
| diaminoisopropane |
| 1,2-diaminoisobutane |
| 1,2-diaminoisopentane |
| Preferred Cyclic Diamines |
| 1,2-diaminocyclohexane |
| 1,2-diaminocyclopentane |
| 1,2-diaminocycloheptane |
| 1,2-diamino, 3-chlorocyclohexane |
| 1,2-diamino, 3-fluorocyclohexane |
| 1,2-diamino, 3-bromocyclohexane |

For completeness of description and ease of understanding, each of the requisite components comprising the inhibitory analogue substrate composition will be described individually hereinafter. Subsequently, the various ways of preparing and using the analogue substrates as anti-fibrotic agents will be reviewed in detail. Finally, a limited number of laboratory scale experiments will be described to provide empirical data and results illustrating the variety of therapeutic uses and applications for the present invention.

The Organic Supporting Structure Comprising At Least Two, Adjacently Positioned Primary Amine Groups The chemical structure of the inhibitory anti-fibrotic agent is based upon the presence of an organic supporting structure - a carbon backbone having at least two adjacently positioned carbon atoms available for the attachment of primary amine groups. These organic supporting structures and their derivatives may comprise saturated and/or unsaturated molecules; straight and branched linear chains; single and multiple rings any combination of these as monomers, dimers, and polymers. In addition, each of these organic supporting structures may also contain substituted hydrocarbons and organic groups to form derivatized forms.

Each preferred organic supporting structure encompassed by Formula I will support at least two adjacently positioned primary amine groups in a manner which permits an enzyme analogue substrate of lysyl oxidase to be formed. Clearly therefore, at least two adjoining primary amine groups available for reaction must always be present in these embodiments. In some instances, three or more primary amine moieties might also be effectively utilized in more intricate and involved molecular arrangements and organizational networks. In most embodiments, however, it is more desirable that the diamine derivative form by employed. To demonstrate the variety of different organic supporting structures able to employed in diamine and polyamine derivatized form, a representative but incomplete listing of supporting backbone structures deemed to be useful in the present invention is provided by Tables II, III, and IV respectively below.

TABLE II

| ORGANIC STRUCTURE | BACKBONE STRUCTURE | DIAMINE DERIVATIVE |
|---|---|---|
| ethane | $\text{R—CH}_2\text{—CH}_3$ | $\text{R—CH(NH}_2\text{)—CH}_2\text{—NH}_2$ |
| butane | $\text{CH}_3\text{—CH}_2\text{—CH}(\text{—CH}_2\text{—R})$ | $\text{CH}_3\text{—CH(NH}_2\text{)—CH(NH}_2\text{)—CH}_2\text{—R}$ |
| heptane | $\text{CH}_3\text{—CH}_2\text{—CH}_2\text{—CH(—CH}_2\text{—CH}_2\text{—CH}_2\text{—R)}$ | $\text{CH}_3\text{—CH}_2\text{—CH(NH}_2\text{)—CH(NH}_2\text{)—CH}_2\text{—CH}_2\text{—CH}_2\text{—R}$ |
| 2-pentene | $\text{CH}_3\text{—CH=CH—CH}_2\text{—CH}_2\text{—R}$ | $\text{CH}_3\text{—CH=C(NH}_2\text{)—C(NH}_2\text{)—CH}_2\text{—CH}_2\text{—R}$ or $\text{CH}_3\text{—CH=CH—CH(NH}_2\text{)—CH(NH}_2\text{)—R}$ |
| 2,4-hexadiene | $\text{CH}_3\text{—CH=CH—CH=CH—CH}_2\text{—R}$ | $\text{CH}_3\text{—CH=C(NH}_2\text{)—C(NH}_2\text{)=CH—CH}_2\text{—R}$ | including a variety of heterocyclic ring structures; and

TABLE III

| ORGANIC SUPPORT | BACKBONE STRUCTURE | DIAMINE DERIVATIVE |
|---|---|---|
| cyclopropane | $\text{H}_2\text{C—CH(R)—CH}_2$ (ring) | $\text{H}_2\text{N—CH—CH(R)—CH—NH}_2$ (ring) |

TABLE III-continued

| ORGANIC SUPPORT | BACKBONE STRUCTURE | DIAMINE DERIVATIVE |
|---|---|---|
| cyclohexane | R-CH with cyclohexane ring | R-CH with cyclohexane ring bearing two adjacent -NH$_2$ groups |
| dicyclohexane | decalin with R | decalin with R and two adjacent -NH$_2$ groups |
| 1,4-cyclopentadiene | R-C cyclopentadiene ring | R-C cyclopentadiene ring with two -NH$_2$ groups |
| 4,6-cyclohexadiene | R-C cyclohexadiene ring | R-C cyclohexadiene ring with two -NH$_2$ groups |

TABLE IV

| ORGANIC SUPPORT | BACKBONE STRUCTURE | DIAMINE DERIVATIVE |
|---|---|---|
| phenyl ring and phenyl derivatives | cyclohexane ring with R | cyclohexane ring with R and two adjacent -NH$_2$ groups |
| napthalene and napthalene derivatives | decalin with R | decalin with R and two -NH$_2$ groups (1,2-position) or decalin with R and two -NH$_2$ groups (2,3-position) |
| quinoline and quinoline derivatives | decahydroquinoline with R and NH | decahydroquinoline with R, NH and two -NH$_2$ groups or isomer with R, NH and two -NH$_2$ groups |

TABLE IV-continued

| ORGANIC SUPPORT | BACKBONE STRUCTURE | DIAMINE DERIVATIVE |
|---|---|---|
| indole and indole derivatives | 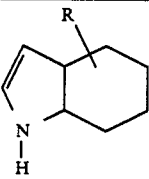 | 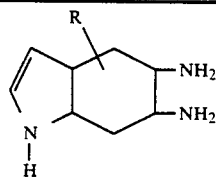 |
| phenanthrene and phenanthrene derivatives | 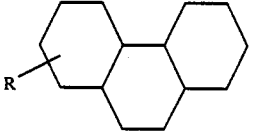 | 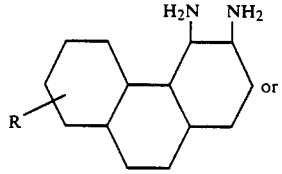 or 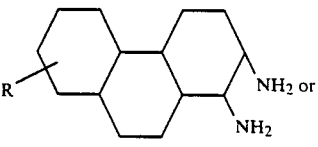 |

Table II illustrates some of the saturated and unsaturated organic support structures and their respective diamine derivatized forms wherein R is selected from the group consisting of hydrogen, an inorganic entity, and an organic moiety. It will be appreciated that the two primary amine groups are always positioned on adjacent carbon atoms when employing any of the alkyl support structure regardless of the total number of carbon atoms in the molecule as a whole.

Similarly, when unsaturated moieties form part of the organic support structure, it is most desirable that the molecular configuration assume a cis orientation rather than a trans orientation in order that the primary amine groups be aligned in the same stereochemical plane. It will be recognized by ordinary practitioners in this art that the saturated organic support structures as a class offer a greater number of rotational degrees of freedom in comparison to unsaturated, olefin support structures. Nevertheless, straight and branched linear chains comprising hydrocarbons or substituted organic saturated molecules will provide many useful and operative support structures as backbone components in the present invention.

Table III illustrates a variety of saturated and unsaturated cyclic molecular arrangements and diamine derivatives. Clearly, the number of degrees of rotational freedom provided by cyclic structures is more limited in comparison to linear and branched chain arrangements having the same number of carbon atoms. It is desirable also that each attached primary amine group lie in a cis orientation rather than a trans orientation with respect to at least one other adjacently positioned primary amine group in the overall structure. For descriptive purposes, however, the primary amine groups of Table III are attached to adjacently positioned carbon atoms without orientational specificity in each instance. In addition, the positioning of primary amine groups on adjacent carbons within a ring structure is an absolute requirement. A variety of alternative arrangements are illustrated by Table IV in which the organic supporting structures are all cyclic ring structures in nature and are deemed to represent all aromatics and/or aryl derivatives without limitation. It will be appreciated that while the two primary amine groups are attached to adjacent carbon atoms in the single phenyl ring structure, the napthalene and quinoline structures individually permit attachment of adjacently positioned primary amine groups at different locations on the ring structure. Furthermore, the 3-ring structure of phenanthrene allows the user to position the two primary amine groups upon adjacent carbon atoms at various positions within the multi-ring organization.

The requisite principle and sole limiting factor is that the organic supporting structure provide at least one pair of adjacently positioned carbon atoms for the attachment of two primary amine groups such that a discrete, identifiable diamine composition is formed. The true formula and sterochemical arrangement of the supporting structure, the placement of the two adjacently positioned amine groups within the support structure, and the true total number of primary amine groups within the composition are not paramount or decisive; rather, these are secondary and tertiary factors which affect the ease of preparation, effective use concentration, and inhibitory efficacy of the resulting substrate analogue.

It will be recognized and appreciated also that the chemical structure of Formula I is defined broadly to encompass all possible useful sizes, structures, moieties, constituents, and chemical formulations of carbon and other atoms which are believe able to demonstrate at least some measurable inhibitory effect on the enzymatic activity of lysyl oxidase, given the presence of its co-factor, pyrroloquinoline quinone (PQQ), in-situ. For these reasons also, the stated definitions of Y, Y', Z, Z', W, R and J are given broadly, rather than narrowly, to insure that the many structural variations, formulations, and derivative forms known for organic structures are included.

Moreover, the subject matter as a whole comprising the present invention is provided as a discrete, integral, preformed enzyme substrate analogue which is intended to be prepared in advance and expected to be used as an antifibrotic agent in-vivo. For this reason, the preferred embodiments are simple chemical structures and formulas. However, the simpler forms may be joined to many different ligands obtained from diverse sources and origins if more complex embodiments are desired. The intended manner of covalently attaching the diamine composition of Formula I is via an organic moiety identified as "R" in the most general definitions of the present invention; and preferably are the entities provided by Table V in the majority of instances.

TABLE V

| CHEMICAL STRUCTURE | "R" ENTITY |
|---|---|
| —COOH | Carboxyl |
| —$N_3$ | Azide |
| —C(=O)—ON(succinimide) | N-Hydroxysuccinimide esters |
| —$NH_2$ | Amine |
| —OH | Hydroxyl |
| —SH | Thio |
| —NCS | Isothiocyanate |
| —C≡N | Nitrile |
| —F, —Cl, —Br, —I | Halogens (fluoro, chloro, bromo, iodo) |

It will also be recognized and appreciated that the organic supporting structure comprising at least two adjacently positioned primary amine groups, regardless of the formula and internal structure of the molecule, may be usefully employed in a variety of different formats—that is, as a monomer, a dimer, or a polymerized molecule. For illustrative purposes only, this discussion will focus upon and be limited to a branched saturated composition having two primary amine groups such as is provided by Table VI below.

TABLE VI

| FORMAT | POLYAMINE STRUCTURE |
|---|---|
| monomer | $R_3-C(R_1)(H_2N)-C(R_2)(NH_2)-R_4$ |
| dimer | $R_3-C(R_1)(H_2N)-C(R_2)(NH_2)-R_4-R_7-C(R_5)(H_2H)-C(R_6)(NH_2)-R_8$ |
| polymer | $[R_3-C(R_1)(H_2N)-C(R_2)(NH_2)-R_4]_q-J-[R_7-C(R_5)(H_2N)-C(R_6)(NH_2)-R_8]_t$ | wherein $R_1$–$R_8$ individually are selected from the group consisting of hydrogen, a hydrocarbon moiety, a halogen, and an organic group;

J is a linking molecule; and q and t individually are zero or a positive integer.

The monomer format of Table VI follows and includes all the examples previously given by Table II (and inherently Tables III and IV as well). The dimer format of Table VI is a covalent linking of two monomer units which may or may not be identical in composition. The reactions and reagents employed in preparing the dimer format are conventionally known in the scientific literature and are easily adapted to link any combination of individual monomer units. The polymer format of Table VI envisions and intends the use of a cross-linking agent identified generally as "J"; and also recognizes that each copolymer may itself be prepared as a homopolymer prior to cross-linking with the other copolymer. In addition, it is intended that each prepared homopolymer be useful in its own right without further cross-linking to another copolymer—if this is either desirable or necessary for the user. Methods, reactions, and reagents are conventionally known for preparing both homopolymers, and cross-linking individual copolymers. All of these conventionally known formats and techniques may be freely employed as desired when preparing a particular organic support structure comprising a plurality of primary amine groups for use in the present invention.

Therapeutic Applications

The inhibitory analogues substrates of Formula I are deemed to provide therapeutic benefits in-vivo when administered to living subjects, humans and animals, afflicted with a pathological fibrotic state. These inhibitory analogue substrates can serve as chemotherapeutic agents to prevent, lessen, and/or control the development of fibrosis in such diseases as: lung fibrosis, atherosclerosis, keloid, liver fibrosis, scar formation, diabetes, tumor development, and post-operatively in procedures such as radial keratotomy where scar formation is counterproductive to the purposes of the surgery.

Routes Of Administration In-Vivo

Compounds embodying Formula I of the invention can be administered in any appropriate carrier for oral, topical, inhalatory, or parenteral administration. They can be introduced by any means that effects conditions of fibrosis in living humans or animals. The dosage administered will vary and be dependent upon the age, health, and weight of the recipient; the kind of concurrent treatment, if any; the frequency of treatment; and the nature of the therapeutic effect desired. Generally, the expected daily dosage of an inhibitory substrate analogue will be from about 0.01 milligrams/kg to 1.0 milligrams/kg, the true dosage and best route of administration to be established after thorough assessment of potential toxicity, inhibitory potency, and efficacy.

Normally, from 0.5 to 50.0 milligrams per day, in one or more administrations per day, is expected to be therapeutically efficacious to yield the desired beneficial results.

If the inhibitory substrate analogues prepared in accordance with Formula I are to be applied topically, they can be admixed in a pharmacologically inert topical carrier such as a gel, an ointment, a lotion, or a cream; and include such carriers as water, glycerol, alcohol, propylene glycol, fatty alcohols, triglycerides, fatty acid esters, or mineral oils. Other possible topical carriers are liquid petrolatum, isopropylpalmitate, polyethylene glycol ethanol 95%, polyoxyethylene monolaurate 5% in water, sodium lauryl sulfate 5% in water, and the like. Materials such as anti-oxidants, humectants, viscosity stabilizers, and the like may be added, if necessary.

In contrast, administration by inhalation will utilize pressurized gases, propellants, and emulsifiers. Also, the inhibitory substrate analogue composition may be disposed within devices placed on, in, or under the skin; such devices include patches and implants which release the active material into the skin or body either by diffusion or by an active release mechanism.

Similarly, if the inhibitory substrate analogues of Formula 1 are to be given parenterally, they will be prepared in sterile form; in multiple or single dose formats; and dispersed in a fluid carrier such as sterile physiological saline or 5% dextrose solutions commonly used with injectables.

To demonstrate the utility, enzyme specificity, and efficacy of the therapeutic methodology comprising the present invention, a variety of experiments and empirical data will be described hereinafter. It will be expressly understood, however, that these experiments and empirical results are merely descriptive of the present invention as a whole; and serve to merely illustrate some situations in which the present invention may be usefully employed. None of the experimental modes, empirical data, or conclusions are deemed to be restrictive of the invention in any form or use; to the contrary, it will be recognized and appreciated that these experiments merely demonstrate the variety of applications and the range of effective parameters one may expect to be in effect when employing the present invention.

Empirical Experiments

A. Materials and Methods

Reagents

Homovanillic acid, horse radish peroxidase, n-hexylamine, 1,6-diaminohexane, ethylenediamine, 1,5-diaminopentane, and n-propylamine were obtained from Sigma Corp. The cis and trans isomers of 1,2-diaminocyclohexane were obtained from Alfa Products. [$^3$H]NaCNBH$_3$ (10 Ci mmole$^{-1}$) was a product of Amersham Corp. Pyrroloquinoline quinone was obtained from Fluka Corp.

Enzyme Purification

Lysyl oxidase was purified from bovine aorta as previously described. [Williams, M. A. and H. M. Kagan, *Anal. Biochem.* 113:336 (1985)]. The resulting preparation consists of a copurified mixture of four ionic variants of lysyl oxidase. Each of these enzyme variants has a molecular weight of 32,000 in sodium dodecylsulphate; peptide maps of proteolytic digests of the individual variants are very similar; and the substrate specificities and inhibition profiles of the variants appear to be virtually the same. This indicates that the catalytic mechanism is likely to be the same for each of these enzyme forms [Sullivan, K. A. and H. M. Kagan, *J. Biol. Chem.* 257:13520–13526 (1982)].

The purified lysyl oxidase was assayed against an insoluble elastin substrate prepared from chick embryo aortas which had been pulsed in organ culture with L-[4,5-$^3$H]lysine [Kagan, H. M. and K. A. Sullivan, *Methods Enzymol.* 82A:637–649 (1982)]. Enzyme assays include 125,000 cpm of the elastin substrate in 0.1M sodium borate, 0.15M sodium chloride at pH 8.0 in a total volume of 750 ul and were incubated for 2 h at 37° C. Tritiated water formed during the incubation was isolated by vacuum distillation and quantified by liquid scintillation spectrometry of 0.5 ml aliquots of the distillates. All activities were corrected for enzyme-free controls and were within the linear range of this assay (100 to 1200 cpm released per 2 h). One enzyme unit was defined as 1 dpm of $^3$H released by enzyme action in 2 h. Functional active site content was quantified by comparing the specific activity of each enzyme preparation against the elastin substrate to the theoretical, maximum value of $4 \times 10^6$ u mg$^{-1}$ previously estimated as the value for the fully functional enzyme [Williamson et al., *Biochem. J.* 235:597–605 (1986)].

The purified lysyl oxidase enzyme was also assayed against alkyl monoamines and alkyl diamines using the reported peroxidase-coupled fluorescence method at 55° C. [Trackman et al., *Anal. Biochem.* 113:336–342 (1981)]. The reaction mixtures contained 40 ug horseradish peroxidase, 0.7 mM homovanillic acid, 1.2M urea, 0.02M potassium phosphate/borate buffer, at pH 8 (or at varying values of pH as indicated) in a total volume of 2 ml. Assay solutions were adjusted to an ionic strength of 0.04 using potassium chloride. Lysyl oxidase was then added to initiate the reaction. Fluorescence was continuously monitored at an excitation wavelength of 315 nm and an emission wavelength of 425 nm. The enzyme-dependent production of hydrogen peroxide was quantified by reference to standard plots relating nanomoles of hydrogen peroxide added to fluorescence units. Assays carried out at a pH which occurred within the overlapping buffering ranges of phosphate and borate resulted in the same value of Vmax regardless of the presence of the phosphate, of the borate, or of both buffering species. Kinetic constants were derived from initial rate assay data by using the Fortan program of Cleland [*Meth. Enzymol.* 63:103–138 (1979)] which determines Vmax and Km values from data of Michaelis-Menten experiments using a least squares fitting procedure applied to the Michaelis-Menten equation.

Spectral Studies

Absorption spectra were recorded in 1 cm cuvettes with a Hewlett Packard Diode Array spectrophotometer, with temperatures controlled by circulating water through the cuvette holder. Mixtures were made anaerobic by purging buffers and stock solutions in rubber-capped tubes with high purity nitrogen for 15 min, and then injecting aliquots of the solutions into a 1 cm semimicro cuvette fitted with a rubber septum and flushed with nitrogen before addition of reagents. Once in the capped cuvette, each solution was further exposed to a stream of nitrogen passed over the surface of the solution and out of the capped cuvette through 21 guage needles for 5 min. just prior to spectral recording. Each perturbation described was reproducible in three or more trials.

NMR spectra were obtained on a Bruker AC 200 spectrometer. Solutions for NMR studies were prepared in $D_2O$ and the pH was adjusted to 8.0 with NaOD. Solutions containing 10 mM PQQ were prepared in the presence or absence of 9 mM ethylenediamine or of 9 mM concentrations of the cis or trans isomers of 1,2-Diaminocyclohexane or "DACH". The presence of 40 mM sodium borate did not affect the spectra. The HOD peak was suppressed by homonuclear decoupling. Chemical shifts are referenced to sodium 3-trimethylsilyl[$2,2,3,3-^2H$]propionate as the internal standard.

B. Synthesis of [$1,2-^3H$]-1,2-Diaminocyclohexane

[$1,2-^3H$]-1,2-diaminocyclohexane was synthesized by reductive amination of 1,2-cyclohexanedione according to the method of Borch et al., [*J. Am. Chem. Soc.* 93:2879-2903 (1971)]. A solution of 1,2-cyclohexanedione (5 mmol), ammonium acetate (100 mmol), and [$^3H$]NaCNBH$_3$ (7 mmol; 230 uCi mmole$^{-1}$) in 30 ml of absolute methanol was stirred at 25° C. for 48 h. The pH was then adjusted to pH 1.5-2 with 12N HCl; the solution brought to dryness; and the residue was taken up in 10 ml of water and extracted with three 20 ml portions of ether. The aqueous layer was then adjusted to pH 10-11 with KOH; solid NaCl was added to saturation; and the solution was then extracted with several 15 ml portions of ether. The combined ether extracts were dried over anhydrous magnesium sulfate, filtered, and evaporated in vacuo. The crude product was crystallized and then recrystallized from ethanol-ethylacetate mixtures, with 300 mg of the purified product finally obtained. Thin layer chromatography of the resulting product using methanol:water (9:1) as the developing solvent revealed one ninhydrin-positive spot with an Rf of 0.65-identical to that of a mixture of authentic cis- and trans-DACH. The product melted at 38°-40° C. (literature 37°-42° C.). This product also perturbed the absorption spectrum of pyrroloquinoline quinone or "PQQ" in a manner identical to that of authentic DACH.

C. Empirical Results

Figure 1B:
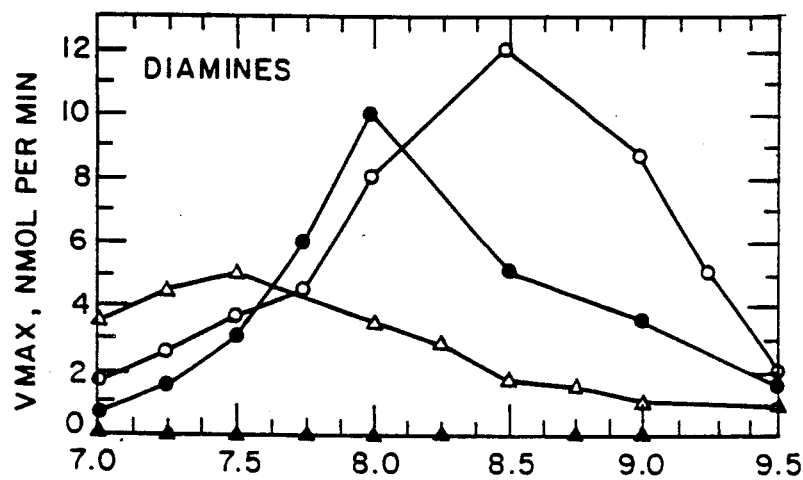

Experimental Series 1: Reaction of Lysyl Oxidase with Monoamine and Diamine Substrates The pH-dependency of the Vmax for the oxidation of a series of diamines and monoamine substrates by lysyl oxidase was first explored. As shown by FIG. 1, the pH optimum shifts to more acidic values as the chain length of diamine substrates is decreased from 6 to 5 to 3 carbons. Moreover, the Vmax values at the pH optima decrease with decreasing chain length and thus the substrate potential decreases with decreasing chain length. Ethylenediamine or "EDA", the shortest of the diamines, proved to be an effective competitive inhibitor of lysyl oxidase activity against n-hexylamine with a $K_I$ of $2\times10^{-6}M$. In contrast to the diamines, the pH optimum remains at approximately 8.5 for monoamines of different chain length as shown in FIG. 1. The Vmax decreases only slightly with decreasing monoamine chain length, contrasting with the marked decrease in Vmax seen with the diamine substrates.

Figure 2:
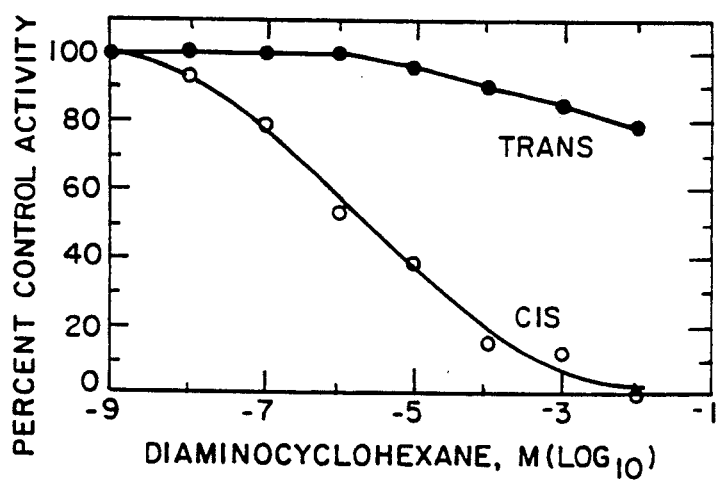
FIG. 2 is a graph illustrating the inhibitory activity of cis and trans isomers of 1,2-diaminocyclohexane upon lysyl oxidase.
Figure 3:
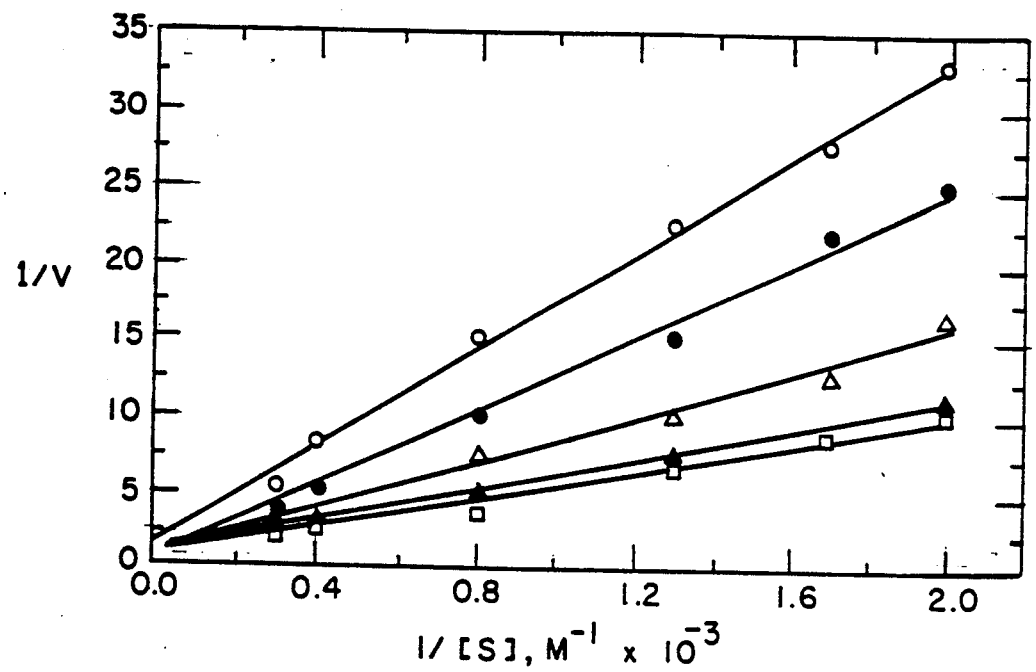
FIG. 3 is a graph illustrating the competitive inhibition of lysyl oxidase activity against n-hexylamine by cis-diaminocyclohexane.

The possibility was then explored that the inhibitory effects of diamines as expressed maximally with EDA may involve the interaction of both of the amino functions of the diamine with an enzyme constituent(s). Since such enzyme groups would likely be specifically oriented relative to each other, it seemed possible that opposite configurational isomers of a sterically restricted diamine might have different reactivities with the enzyme. It is known that benzylamine and its analogues can serve as substrates of lysyl oxidase [Williamson P. R. and H. M. Kagan, *J. Biol. Chem.* 262:14520-14524 (1987)]; and thus it seemed possible that DACH, a saturated cyclic diamine for which the cis and trans isomers are available, possibly could also be accommodated at the active site. Accordingly cis and trans isomers of DACH were used to probe this possibility. As shown in FIG. 2, cis-DACH is revealed to be a potent inhibitor of lysyl oxidase, with an $I_{50}$ of 1.5 $\mu M$ in assays of n-hexylamine oxidation while trans-DACH is at least 10,000-fold less inhibitory with an (extrapolated) $I_{50} > 10$ mM. The differential sensitivity of lysyl oxidase to these agents was virtually the same in assays of [$^3H$]elastin oxidation (not shown). A Lineweaver-Burk plot of the initial rate assays for the mode of inhibition by the cis compound resulted in a series of lines intersecting at the 1/v axis as shown by FIG. 3, indicating that cis-DACH competes with the amine substrate for interaction at the active site. The $K_I$ was calculated from the slopes of this plot and found to be $3.8\times10^{-7}M$. The inhibition by cis-DACH was determined to be irreversible rather than reversible since the lysyl oxidase enzyme (which had been preincubated with 0.05M cis-DACH at 37° for 15 min and then dialyzed to remove the substrate compound) was catalytically inactive.

Figure 4:
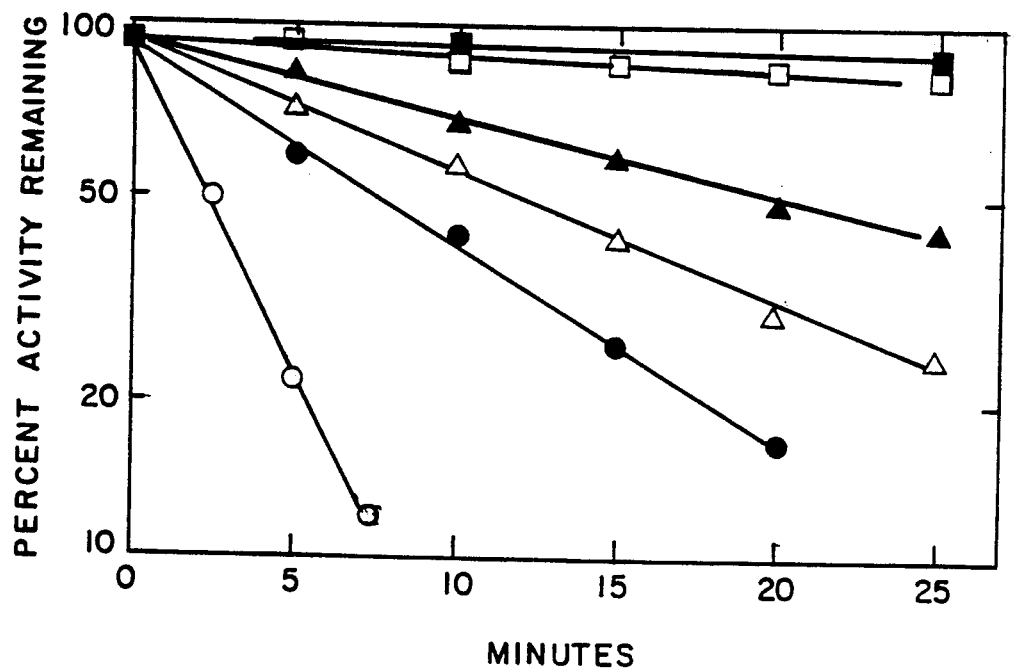
FIG. 4 is a graph illustrating the inactivation of lysyl oxidase by cis-diaminocyclohexane as a First Order reaction.

In addition, the time-dependency for the expression of irreversible inhibition was assessed by initially preincubating lysyl oxidase at 37° in the presence or absence of various concentrations of cis-DACH; and then diluting aliquots of these individual reaction mixtures into peroxidase-coupled assays for n-hexylamine oxidation - thereby reducing the cis-DACH concentrations to non-inhibitory levels within the lysyl oxidase assays. The rates of loss of enzyme activity were found to increase with increasing cis-DACH concentrations, with the inactivation of lysyl oxidase following apparent first order kinetics. This is illustrated by FIG. 4. The limiting apparent first order rate constant for inactivation determined from the intercept of a secondary reciprocal plot of these data was calculated as $K_{inact} = 18$ min$^{-1}$. The possibility that the inactivation derived from the removal of the metal ion cofactor of the enzyme by the cyclic diamine was then assessed by atomic absorption spectroscopy. This method of analysis yielded the same values for protein-bound copper in aliquots of purified lysyl oxidase which had been incubated in either the presence or absence of 1 mM cis-DACH and then dialyzed extensively against metal-free buffer. This data reveals that cis-DACH did not remove copper from the active site in order to cause irreversible inhibition of lysyl oxidase.

Experimental Series 2: Spectral Studies

Figure 5A:
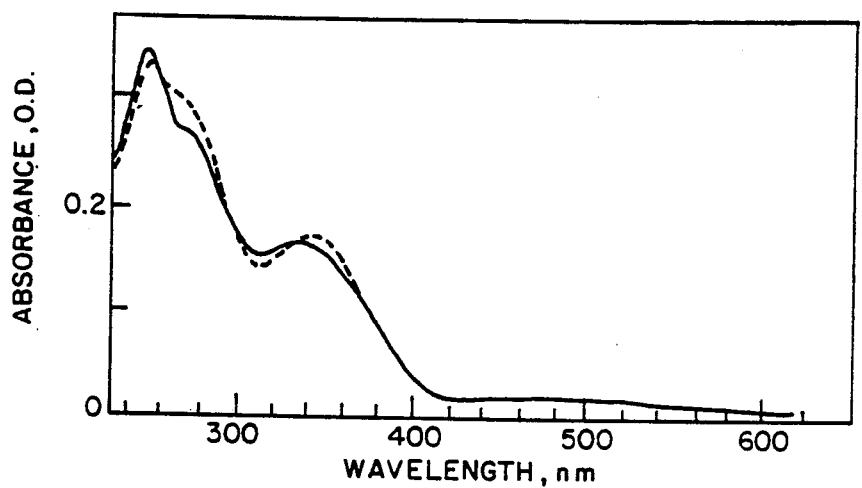
FIGS. 5A, 5B and 5C are graphs illustrating the effects of cis-and trans-isomers of diaminocyclohexane on the absorption spectrum of pyrroloquinoline quinone.
Figure 5B:
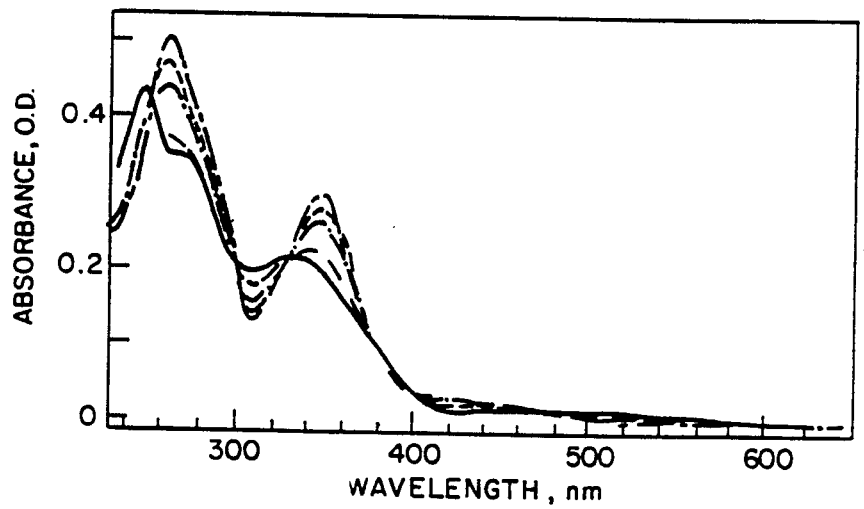

This series of experiments evaluated the possibility that the adjacently positioned primary amino groups of cis-DACH may be interacting with the ortho-carbonyl functions of PQQ in lysyl oxidase. Spectral effects seen with authentic pQQ appeared to support this possibility. As seen in FIG. 5B, the spectrum of PQQ is markedly perturbed by cis-DACH in a time-dependent fashion; in contrast, as seen in FIG. 5A, there is relatively little change generated in the PQQ spectrum by trans-DACH under the same test conditions. This is analogous to the markedly different sensitivities of lysyl oxidase to these isomers individually. Incubation of PQQ with monoamines, including 5 mM cyclohexylamine or 5 mM n-hexylamine, did not perturb the spectrum of PQQ measurably under corresponding conditions (not shown).

Figure 5C:
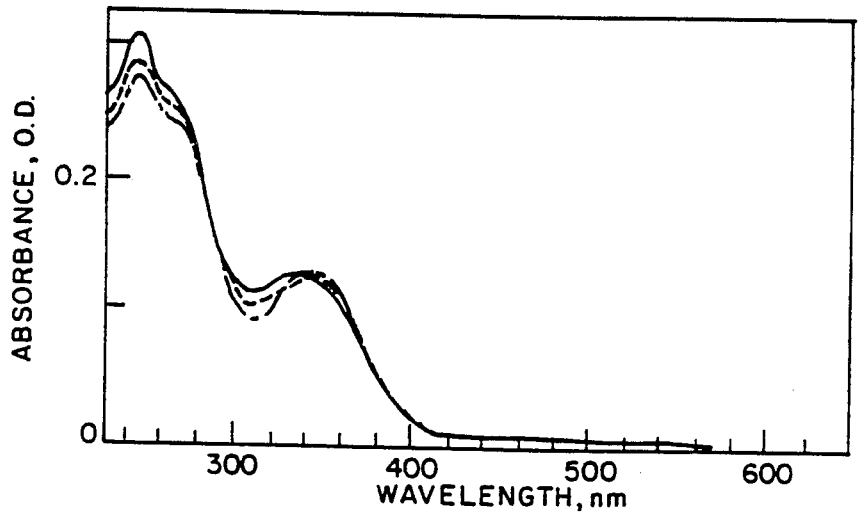
Figure 6B:
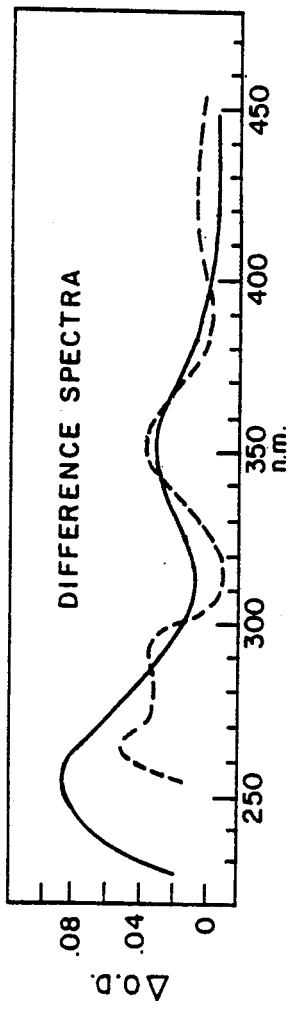
FIGS. 6A and 6B are graphs illustrating the effect of cis-diamino-cyclohexane on the adsorption spectrum of lysyl oxidase.
Figure 6A:
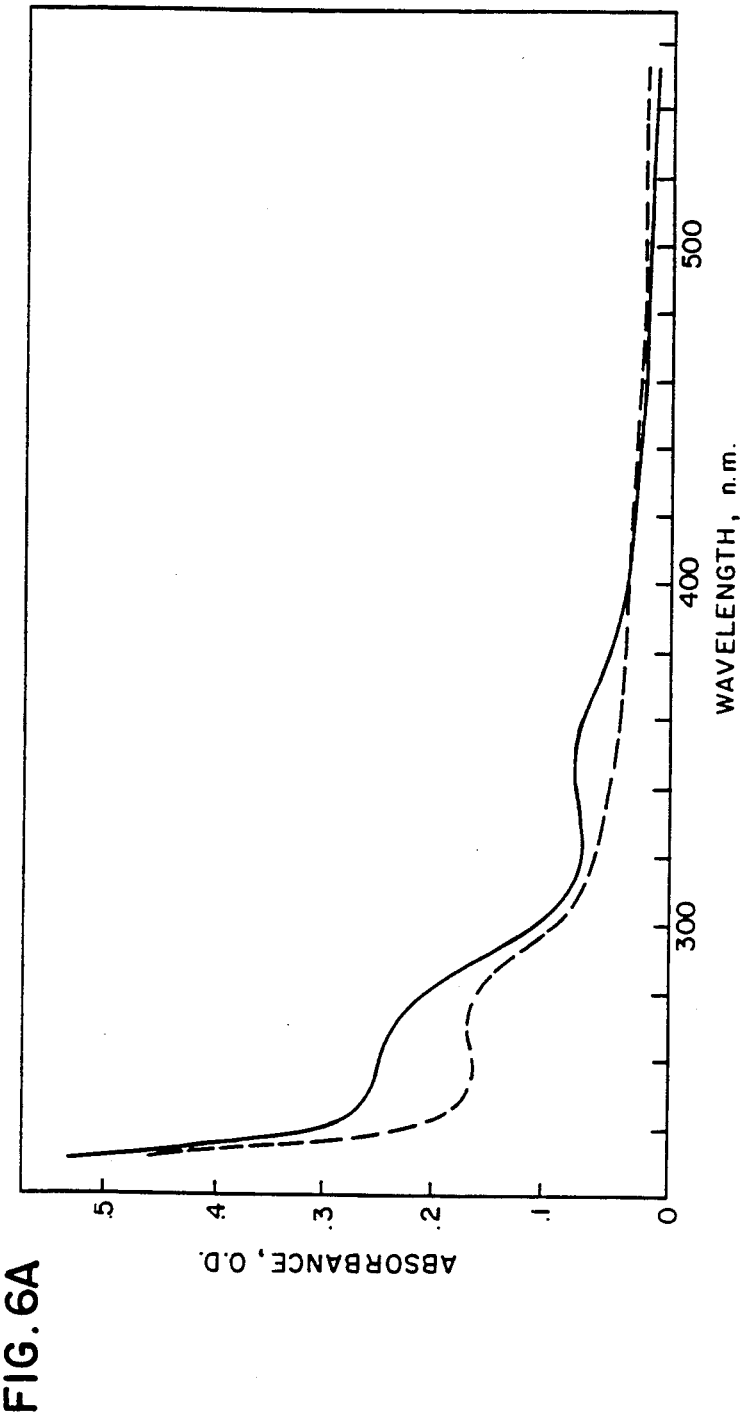

FIG. 5C shows that the perturbation of the spectrum by cis-DACH was dependent upon the presence of oxygen as noted by the relatively small spectral changes induced in the PQQ spectrum under anaerobic conditions. Further, as shown in FIG. 6A, the spectrum of lysyl oxidase is also perturbed upon the addition of the cyclic diamine. Increased absorption occurs in accordance with an increase in optical density occurring in the region of 250 nm; a broad peak also develops with a maximum absorbance at 350–355 nm upon incubation of 47 uM cis-DACH with 4.25 uM of functional active sites in lysyl oxidase as shown in FIG. 6B. The absorption peak at 350–355 nm correlates quite well with a peak generated at the same position in the spectrum of PQQ by its interaction with cis-DACH. In contrast, the spectrum of lysyl oxidase was not altered significantly by cis-DACH under anaerobic conditions.

Experimental Series 3: Dependency of the inhibition Upon Oxygen

Figure 7:
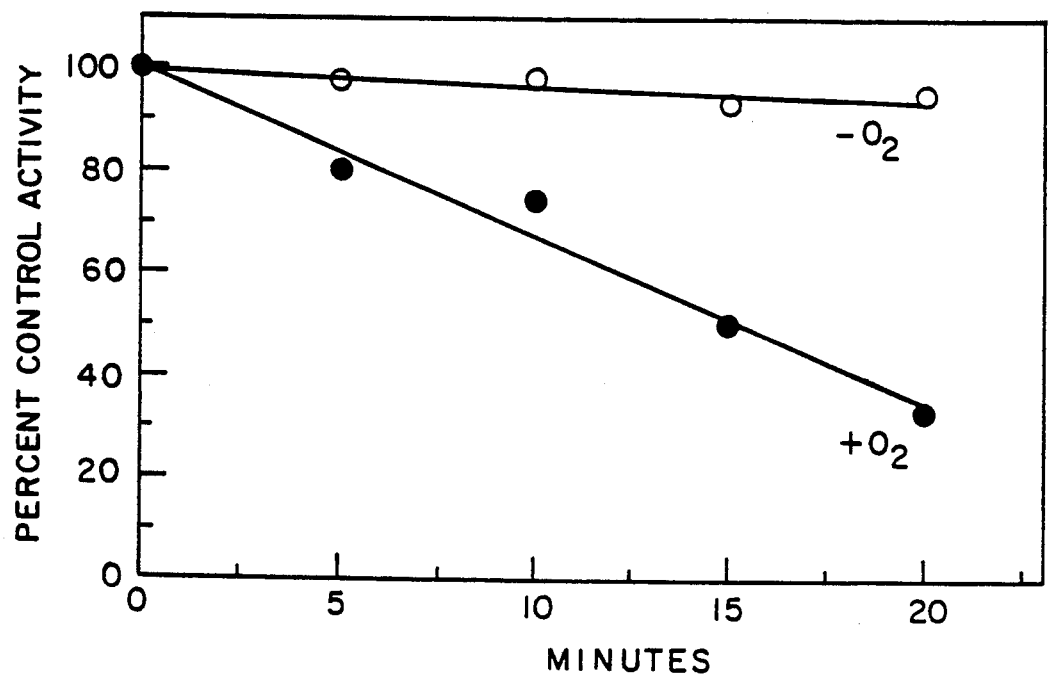
FIG. 7 is a graph illustrating the effect of oxygen on the inactivation of lysyl oxidase by cis-diaminocyclohexane.

In view of the apparent inhibiting effect of anaerobic conditions on the induction by cis-DACH of changes in the spectra of PQQ and lysyl oxidase, the possibility was evaluated that oxidation of the diamine substrate analogue may be involved in the development of irreversible inhibition of lysyl oxidase. In this regard, the formation of $H_2O_2$ was not detectable within the limits of sensitivity (ca. 1 nanomole of $H_2O_2$) if cis-DACH was incubated with catalytic quantities (2–4 ug) of lysyl oxidase in the peroxidase-coupled assay for $H_2O_2$ release. This argues against significant catalytic turnover with the cyclic diamine. Nevertheless, as illustrated by FIG. 7, the development of irreversible inhibition was strongly dependent upon the presence of oxygen since the rate of inactivation was negligible under anaerobic conditions.

Although cis-DACH did not appear to be a productive substrate, one might question whether indications of cis-DACH oxidation by the free cofactor or the purified enzyme might be obtained at levels stoichiometric with PQQ or lysyl oxidase active sites. Toward that end, evidence was sought for the release of $H_2O_2$ upon the reaction of cis-DACH with limiting amounts of PQQ or of relatively large quantities (although limiting relative to cis-DACH) of pure lysyl oxidase. As given by Table E1, hydrogen peroxide formation was seen under these conditions with the maximum levels of $H_2O_2$ formed essentially equal to the amount of the limiting reactant in both cases, i.e., free PQQ or lysyl oxidase, respectively.

TABLE E1

| Oxidation of cis-DAH: Release of $H_2O_2$[a] | | | |
|---|---|---|---|
| Oxidant | Nanomoles of Oxidant | $H_2O_2$ Released (nanomoles) | Ratio $H_2O_2$/Oxidant |
| PQQ | 13.2 | 14.2 | 1.08 |
| | 26.4 | 24.6 | 0.93 |
| | 52.8 | 51.2 | 0.97 |
| | 79.2 | 74.9 | 0.95 |
| | | | $\bar{X} = 0.98 \pm 0.07$ |
| Lysyl Oxidase | 0.71 | 1.0 | 1.40 |
| | 1.78 | 1.70 | 0.96 |
| | 2.20 | 1.52 | 0.69 |

TABLE E1-continued

| Oxidation of cis-DAH: Release of $H_2O_2$[a] | | | |
|---|---|---|---|
| Oxidant | Nanomoles of Oxidant | $H_2O_2$ Released (nanomoles) | Ratio $H_2O_2$/Oxidant |
| | | | $\bar{X} = 1.02 \pm 0.29$ |

[a] Hydrogen peroxide as assayed in the peroxidase-coupled fluorescence assay using 1 mM cis-DACH as the sole source of amine substrate and containing lysyl oxidase or PQQ at the indicated amounts. Incubations were continued until the release of $H_2O_2$ was maximal in each case. The quantity of lysyl oxidase used is expressed in the Table in terms of functional active site content. The concentration of PQQ was determined from the $A_{257}$, using 19,122 as the molar extinction coefficent.

TABLE E2

| Oxidation of [1,2-$^3$H]DACH: Release of $^3H^+$[a] | | | |
|---|---|---|---|
| Oxidant | Nanomoles of Oxidant | $^3H^+$ Released (Nanomoles) | Ratio $^3H^+$/Oxidant |
| PQQ | 2.1 | 5.1 | 2.43 |
| | 4.0 | 9.0 | 2.30 |
| | 6.0 | 13.0 | 2.17 |
| | 7.5 | 17.2 | 2.29 |
| | | | $\bar{X} = 2.3 \pm 0.11$ |
| Lysyl Oxidase | 0.50 | 0.98 | 1.96 |
| | 1.24 | 2.23 | 1.80 |
| | 3.72 | 6.95 | 1.87 |
| | | | $\bar{X} = 1.88 \pm 0.07$ |

[a] The indicated amounts of PQQ or functional active sites of lysyl oxidase were incubated with [$^3$H]DACH (1 mM; 0.13 mCi/mmole) in 50 mM sodium borate, pH 8, at 37°C. and aliquots of the incubation mixture were removed at intervals, distilled in vacuo and the isolated [$^3$H]H$_2$O was quantified by liquid scintillation spectrometry. The values shown are the maximum levels accumulated in these assays and are corrected for minor background effects in the absence of oxidant.

Toward similar ends [1,2-$^3$H]DACH was synthesized and used to determine whether the reaction of this diamine with limiting quantities of free PQQ or of lysyl oxidase would result in the release of $^3H^+$—a result to be expected if carbon 1 and/or carbon 2 positions of cis-DACH were oxidized in these reaction mixtures. As provided by Table E2, approximately 2 moles of $^3H^+$ were released per mole of each limiting reactant; with a maximum of 2.30 moles of $^3H^+$ released per mole of PQQ and a maximum of 1.88 moles of $^3H^+$ released per mole of functional active site in lysyl oxidase. While the synthetic, tritiated product used in these studies consisted of a mixture of the cis and trans isomers, the concentration of [$^3$H]DACH incubated with the lysyl oxidase enzyme was sufficiently low to restrict the reaction primarily to the cis isomer—based upon the previous assessment of the relative potency of these compounds as inhibitors of lysyl oxidase or as perturbants of the spectrum of PQQ.

Experiment Series 4: NMR Spectral Analysis

Initially solutions containing PQQ and a 0.9 molar equivalent of EDA or cis-DACH were incubated at pH 8 in $D_2O$ at 25° C. for 24 h to insure completion of the reaction and the mixture was analyzed by $^1H$ nuclear magnetic resonance spectroscopy. The NMR spectrum of PQQ incubated in the absence of ligands exhibited peaks at 8.25 (H-8) and 7.16 ppm (H-3) due to the presence of the carbonyl form of PQQ to the extent of 60% of the total cofactor present; and at 8.16 (H-8) and 7.17 (H-3) ppm due to the water adduct (40%) at C-5. The spectrum of EDA in the absence of PQQ contained a single peak at 3.03 ppm deriving from aliphatic hydrogens. The cis and trans isomers of DACH showed identical NMR spectra with resonances at 2.83 (t, 2H) due to H-1 and H-2; 2.03 (t, 1H) and 2.00 (s, 1H) due to axial H-3 and H-6; and at 1.77 ppm (t, 2H) due to equatorial H-3 and H-5.

No resonances were seen in the aliphatic region after complete reaction between with PQQ and EDA. Resonances for the complex were seen only at 7.34 (s, 1H, H-3), 8.30 (s, 1H, H-8), 8.73 (s, 1H) and 8.69 ppm (s, 1H) ppm—the latter two deriving from new aromatic protons generated during the reaction. Thus, two protons either were lost or had exchanged with deuterium from the solvent. After complete reaction with cis-DACH, resonances were observed in the aromatic region at 7.28 (s, 1H, H-3) and 8.31 (s, 1H, H-8); and in the aliphatic region at 3.01 (s, 2H), at 2.90 (s 2H) and at 1.96 ppm (s, 4H). As had been observed in the EDA-PQQ mixture, two protons of the cyclic diamine reactant also were lost or had exchanged with solvent. NMR spectra obtained for reactions incubated under anaerobic conditions evidenced a complex distribution of intermediates and/or products; and exhibited very broad aliphatic proton resonances in further contrast to the aerobic results.

In the course of these studies, spectral and kinetic comparisons were made between the reactions of cis-DACH and of EDA with PQQ with the lysyl oxidase. Ethylenediamine was found to induce the same spectral changes in free PQQ as was true of cis-DACH. Moreover, the spectral perturbations as well as the rate of inactivation were all markedly reduced in a nitrogen-purged atmosphere, again consistent with the behavior of the cyclic diamine.

D. Summary and Conclusions

The empirical results show that cyclic or linear adjacently positioned diamines can be potent inhibitors of lysyl oxidase by virtue of their interaction with PQQ. The decrease in Vmax and in pH optimum seen as the carbon chain length of linear diamines decreased can be viewed as the inhibitory consequences of the development of charge-charge repulsion as well as the alteration in steric disposition of the amino groups of the shorter diamines. Thus, the $pK_a$ values of the amino groups of 1,6-diaminohexane are 10.3 and 11.2 while those of EDA are 7.0 and 10.0.

The importance of the steric factor in diamine-lysyl oxidase interactions is seen in the high specificity for the cis rather than the trans isomer of DACH. The $K_I$ for cis-DACH (0.38 μM) is also signficiantly less than that for EDA (2 μM) indicative of the favorable effect of restriction of rotation about the C—C bond in the cyclic compound. These considerations, as well as the observations that spectral perturbations of free PQQ seen with cis-DACH and EDA are apparently identical while such perturbations were not seen under aerobic conditions with monoamines regardless of chain length, further argue that both amino functions of the diamine react with PQQ.

It appears, however, that simple bifunctional Schiff base formation between the adjacently positioned primary diamine and PQQ is not sufficient to account for enzyme inactivation. Thus, oxidative processing of the bound diamine appears to be necessary to inactivate the enzyme or to perturb the spectrum of free PQQ markedly. The stoichiometry of hydrogen peroxide release accompanying incubation of the vicinal diamine with the enzyme or with free PQQ indicates that oxidative turnover is negligible or absent. Free PQQ can oxidize monoamines with turnover in oxygen however. Moreover, the NMR spectra revealing the loss of aliphatic hydrogens from the α-carbons of EDA and cis-DACH as well as changes in the chemical shift characterizing the two remaining α-hydrogens of EDA to one consistent with hydrogens linked to aromatic carbons argues that both α-carbons of both vicinal diamines become oxidized under aerobic conditions. The release of two α-protons from cis-[1,2-$^3$H]DACH upon aerobic incubation with lysyl oxidase is also consistent with the oxidation of both α-carbons as inactivation develops in the cis-DACH:enzyme complex.

The analogous behavior of cis-DACH and EDA toward free PQQ and lysyl oxidase argues in favor of the conclusion that PQQ is the diamine target at the active site of the enzyme. This is supported by the similar results indicating oxidation of the inhibitory diamine stoichiometric with levels of PQQ or lysyl oxidase active sites, with results indicating specificity of both free PQQ and lysyl oxidase for reaction with cis- rather than trans-DACH, and with the similar perturbations of the spectra of the enzyme and free cofactor by the cyclic diamine. It seems likely that differences noted between the otherwise similar difference spectra resulting from perturbation of enzyme or free PQQ by cis-DACH reflect the microenvironmental influence of the protein on the bound cofactor possibly including spectrum-perturbing interactions of enzyme-bound PQQ with the copper cofactor.

Mechanism of Irreversible Inhibition Using Diamine Analogue Substrate Compositions The mechanism of irreversible inhibition of lysyl oxidase via its cofactor pyrroloquinoline quinone (hereinafter "PQQ") using adjacently positioned diamine analogue substrates is presented by Reaction Scheme I below.

REACTION SCHEME I (PQQ)

-continued
REACTION SCHEME I

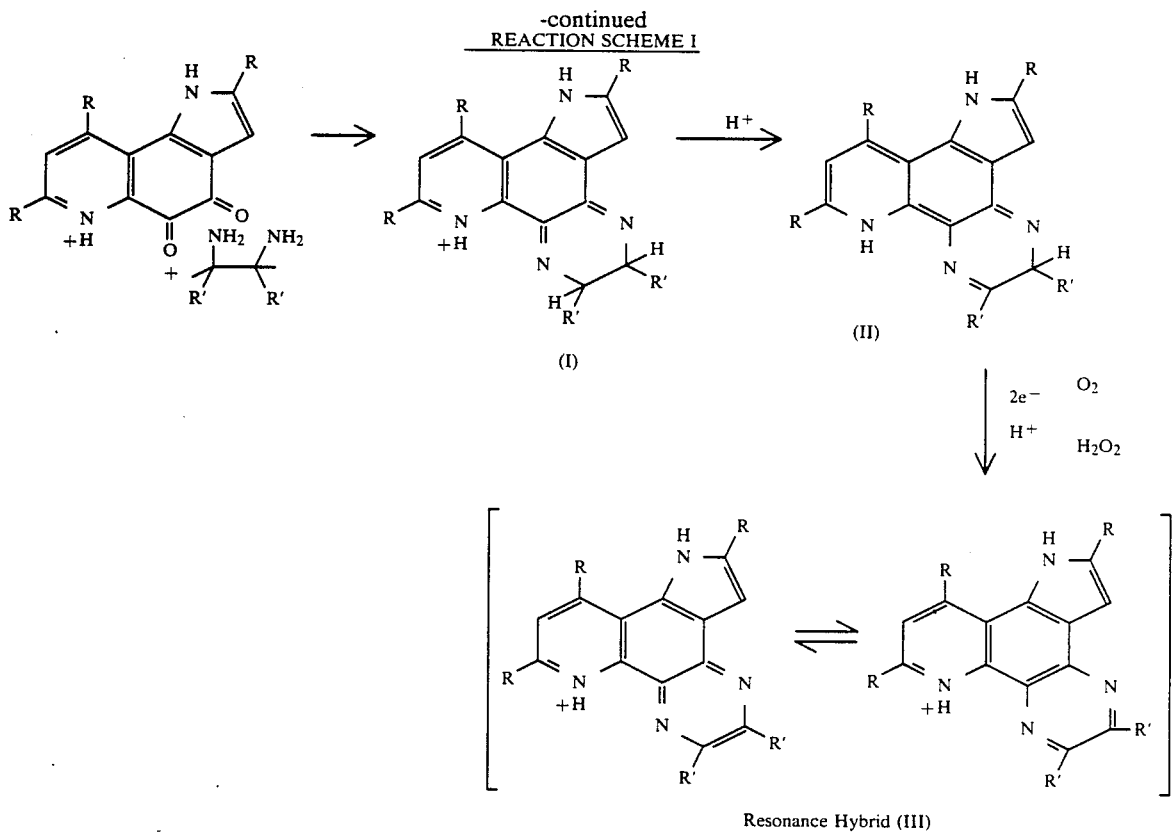

Resonance Hybrid (III)

As seen, both adjacently positioned amino groups of a linear or cyclic diamine can condense to form Schiff bases with the carbonyls of PQQ thus generating a 6-membered ring adduct. Firm conclusions cannot be made at present as to whether the attack of the amino functions on the carbonyls is concerted or sequential. It is noted, however, that of the two carbonyls in PQQ, that at carbon 5 (which is closest to the pyridine moiety) is intrinsically more reactive toward attacking nucleophiles and thus is the first to react with one amino group of the diamine. This is consistent with evidence that monoamine substrates of amino oxidases form a Schifi base at this carbonyl to initiate PQQ-mediate amine oxidation. In this regard, it should also be noted that the development of spectral changes accompanying the aerobic reaction of cis-DACH with PQQ is time-dependent. Plots of the initial rate of change in $A_{350}$ against cis-DACH concentration are consistent with a multicomponent process. However, the minimal change in the spectral under anaerobic conditions argues that separate oxidation steps and not Schiff base formation are the primary causes of the multicomponent kinetics of the spectral changes. In any event, it appears that the oxidation of one α-carbon of the diamine proceeds with the loss of an α-proton and the migration of the exposed electrons of the resultant α-carbanion to yield a reduced derivative of the PQQ-diamine complex one possible form of which is represented by structure II. The abstraction of this proton might involve the assistance of an enzyme general base as appears to be the case in the oxidation of productive substrates by lysyl oxidase. The reaction to this point is able to proceed anaerobically and is also reversible in the absence of oxygen since the electrons introduced into PQQ remain within the conjugated system of the PQQ-diamine complex. This is consistent with the marked diminution in the development of irreversible inhibition of the enzyme seen anaerobically. The reduced PQQ moiety is then reoxidized by transfer of two electrons to oxygen to form one mole of $H_2O_2$ per mole of complex, as found in the present study with both the enzyme and pQQ-inhibitor complex. Once the reduced PQQ derivative is reoxidized, deprotonation of the second α-carbon and migration of the newly exposed electrons from the resultant carbanion could occur resulting in the formation of a conjugated, resonance stabilized 6-membered ring (structure III) joining the diamine and PQQ, thus rendering the complex essentially irreversible and inactivating the enzyme.

The present invention is not to be restricted in form nor limited in scope except by the claims appended hereto:

What we claim is:

1. A method for inhibiting the activity of lysyl oxidase in-situ, said method comprising the steps of:
    combining an effective concentration of at least one potent inhibitory substrate having the formula:

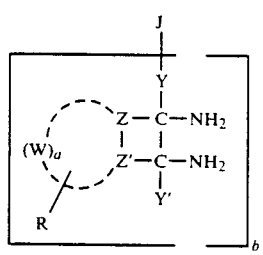

wherein a is 0 or 1 and b is at least 1,

Y and Y, individually may be omitted entirely, but when present are individually selected from the group consisting of hydrogen, a hydrocarbon entity, and a substituted hydrocarbon entity, Z and Z' individually may be omitted entirely, but when present are selected from the group consisting of hydrogen, a hydrocarbon entity, a substituted hydrocarbon moiety, and links R when W is absent, W may be omitted entirely, but when present comprises the number of atoms necessary to form any cyclic structure, R may be omitted entirely, but when present is an organic moiety able to react with another ligand, and J may be omitted entirely, but when present is any organic entity linking the diamine to another molecule as a copolymer, adding with lysyl oxidase and its pyrroloquinoline quinone cofactor in-situ; and allowing said potent inhibitory substrate to interact with said lysyl oxidase and said pyrroloquinoline quinone cofactor whereby said potent inhibitory substrate composition substantially avoids being oxidized and released as a product by said lysyl oxidase and the enzymatic activity of said lysyl oxidase is substantially irreversibly inhibited in-situ.

2. A therapeutic method for treating lysyl oxidase mediated fibrotic disorders in a living subject, said therapeutic method comprising the steps of:

administering at least one potent inhibitory substrate having the formula:

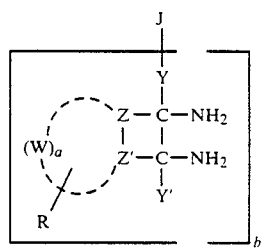

wherein a is 0 or 1 and b is at least 1,

Y and Y' individually may be omitted entirely, but when present are selected from the group consisting of hydrogen, a hydrocarbon entity, and a substituted hydrocarbon entity, Z and Z' individually may be omitted entirely, but when present are selected from the group consisting of hydrogen, a hydrocarbon entity, a substituted hydrocarbon entity, and links R when W is absent, W may be omitted entirely, but when present is any organic moiety able to react with another ligand, and J may be omitted entirely, but when present is any organic entity linking the diamine to another molecule as a copolymer;

to the living subject whereby an effective concentration of said composition combines with such lysyl oxidase and pyrroloquinoline quinone cofactor as are present in-situ; and allowing said potent inhibitory substrate to interact in the living subject with said lysyl oxidase and said pyrroloquinoline quinone cofactor whereby said potent inhibitory substrate composition substantially avoids being oxidized and released as a product by said lysyl oxidase and the enzymatic activity of said lysyl oxidase is substantially irreversibly inhibited in-situ.

3. The method as recited in claim 1 or 2 wherein said inhibitory substrate is a linear diamine.

4. The method as recited in claim 1 or 2 wherein said inhibitory substrate is 1,2-diaminoethane.

5. The method as recited in claim 1 or 2 wherein said inhibitory substrate is a cyclic diamine.

6. The method as recited in claim 5 wherein said inhibitory substrate is diaminocyclohexane.

* * * * *